United States Patent [19]
Berger et al.

[11] Patent Number: 5,091,526
[45] Date of Patent: Feb. 25, 1992

[54] PROCESS FOR THE ENANTIOSPECIFIC SYNTHESIS OF INTERMEDIATES FOR HEXAHYDRO-BENZO[D]-NAPHTHO[2,1-B]AZEPINES

[75] Inventors: Joel G. Berger, Cedar Grove; John W. Clader, Cranford, both of N.J.

[73] Assignee: Schering Corporation, Kenilworth, N.J.

[21] Appl. No.: 635,535

[22] PCT Filed: Jul. 26, 1989

[86] PCT No.: PCT/US89/03166
§ 371 Date: Jan. 8, 1991
§ 102(e) Date: Jan. 8, 1991

[87] PCT Pub. No.: WO90/01476
PCT Pub. Date: Feb. 22, 1990

Related U.S. Application Data

[63] Continuation-in-part of Ser. No. 226,304, Jul. 29, 1988, abandoned.

[51] Int. Cl.$^5$ .............. C07D 223/14; C07C 209/68; C07C 211/42; C07C 209/28
[52] U.S. Cl. .................................. 540/576; 540/596; 540/598; 540/602; 544/145; 544/147; 544/150; 544/153; 544/154; 544/155; 544/157; 544/162; 544/359; 544/380; 546/195; 546/196; 548/517; 548/525; 548/527; 548/528; 548/950; 548/952; 548/953
[58] Field of Search .............. 544/145, 147, 150, 153, 544/154, 155, 157, 162, 359, 380; 546/195, 196; 548/517, 525, 527, 528, 950, 952, 953; 540/576, 596, 597, 598, 602

[56] References Cited

U.S. PATENT DOCUMENTS 4,973,586 11/1990 Berger et al. .................. 514/217

FOREIGN PATENT DOCUMENTS 0064964 11/1982 European Pat. Off. .
0230270 7/1987 European Pat. Off. .

OTHER PUBLICATIONS

Tetrahedron Letters, vol. 22, No. 28, pp. 2633-2636 (1981).
March, J. Advanced Organic Chemistry 3rd Ed., Wiley & Sons, pp. 693-694 (1985).
The Merck Index 10th Ed., pp. 1233-1234 (1983).
Bulletin de la Societe Chimique de France, vol. 12, pp. 4439-4446 (1970).
Berney et al, CA 94-139592d (1981).
Carlsson et al, CA 98-178996r (1983).
Berger et al, CA 108-37669z (1988).
Berger et al, CA 113-145348f (1990).
Takai, CA 113-106396a (1990).

*Primary Examiner*—Cecilia Shen
*Attorney, Agent, or Firm*—Warrick E. Lee, Jr.; Edward H. Mazer; Henry P. Nowak

[57] ABSTRACT

Biologically active, enantiomerically substantially pure intermediates of trans-hexahydro-benzo[d]naphtho[2,1-b]azepines are prepared.

The present invention involves a process for preparing compounds of the general formula 3:

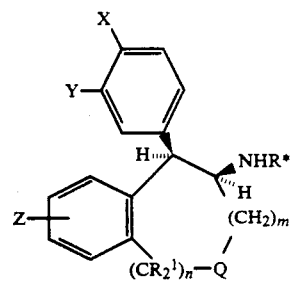

wherein:
R* is

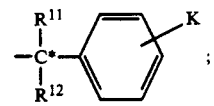

Each $R^1$ is independently H or alkyl;
Q is methylene, —O— or —S—;
m and n are independently variable and may each have a value of 0, 1 or 2, with the provisos that the sum of m and n is not greater than 3, that m may not equal zero when Q is —O— or —S—, and that when Q is —CH$_2$—, m and n cannot both be zero;
X is hydrogen, halo, alkyl, alkylthio, alkylsulfinyl, alkylsufonyl, hydroxy, alkoxy or trifluoromethyl;
Y is hydrogen, hydroxy, alkoxy, —OC(O)NR$^2$R$^3$, —OC(O)—R$^9$, —N(R$^1$)$_2$, —NHC(O)R$^1$ or —OP(O)-(OH)OR$^1$;
$R^2$ and $R^3$ are the same or different and each is hydrogen (provided that both are not hydrogen), alkyl, aralkyl, cycloalkyl, aryl, hydroxyalkyl, or alkoxyalkyl;
in addition, when one of $R^2$ and $R^3$ is as defined above, the other may be —R$^4$NR$^5$R$^6$ {wherein R$^4$ is alkanediyl, R$^5$ is hydrogen or alkyl and R$^6$ is alkyl, or R$^5$ and R$^6$ together with the nitrogen atom form a 1-azetidinyl, 1-pyrrolidinyl, 1-piperidinyl, 1-(4-alkylpiperazinyl), 4-morpholinyl or 1-(hexahydroazepinyl) group};
in further addition, $R^2$ and $R^3$ together with the nitrogen atom may form a 1-azetidinyl, 1-pyrrolidinyl, 1-piperidinyl, 4-morpholinyl, 1-(4-alkylpiperazinyl), 1-(4-alkoxyalkylpiperazinyl), 1-(4-hydroxyalkylpiperazinyl), 1-(3-hydroxyazetidinyl), 1-(3-alkoxyazetidinyl), 1-(-hydroxypyrrolidinyl), 1-(3-alkoxypyrrolidinyl), 1-(3- or 4-hydroxypiperidinyl), 1-(3- or 4-alkoxypiperidinyl), 1-(4-oxopiperidinyl) or 1-(3-oxopyrrolidinyl) ring;
in still further addition, when $R^2$ is hydrogen, $R^3$ may be (Abstract continued on next page.)

—$CHR^7CO_2R^8$, wherein $R^7$ and $R^8$ are the same or different and each is hydrogen, alkyl or aralkyl;

$R^9$ is alkyl, aralkyl, aryl, alkoxyalkyl, aryloxyalkyl, aralkoxyalkyl, cycloalkylalkyl, alkoxycarbonylalkyl, cycloalkyl, 1-adamantyl, cycloalkoxyalkyl, alkoxy, aralkyloxy, cycloalkoxy, aryloxy or —$CHR^7NHR^8$; and Z is X as defined above, amino, alkylamino or —NH-C(O)$R^{10}$ {wherein $R^{10}$ is hydrogen, alkyl or aryl}.

$R^{11}$ is H or alkyl;

$R^{12}$ is alkyl with the proviso that $R^{11}$ and $R^{12}$ are different, and K is hydrogen, alkoxy, hydroxyl, aryloxy or alkyl.

5 Claims, No Drawings

PROCESS FOR THE ENANTIOSPECIFIC SYNTHESIS OF INTERMEDIATES FOR HEXAHYDRO-BENZO[D]-NAPHTHO[2,1-B]AZEPINES

Cross reference to related applications. The present application is the United States national application corresponding to International Application No. PCT/US89/03166, filed July 26, 1989 and designating the United States, which PCT application is in turn a continuation-in-part of U.S. application Ser. No. 226,304, filed July 29, 1988, the benefit of which applications is claimed pursuant to the provisions of 35 U.S.C. 120,363 and 365(c).

BACKGROUND OF THE INVENTION

The present invention relates to a process for the chiral synthesis of enantiomeric intermediates for the biologically trans hexahydrobenzo[d]naphtho[2,1-b]azepines. These compounds have been disclosed as possessing anti-psychotic, anti-depressant and sedative activities in European Patent Application No. 230270. The synthesis described in European Patent Application No. 230270 produces a racemic mixture of the trans and cis amines. It has been found that the trans amine possesses higher biological activity in general than the cis amine. In addition, one enantiomer of the trans amine possesses considerably greater activity than the other. A chiral synthesis producing only a single enantiomer of the trans amine would therefore increase the yield of the biologically more active enantiomer by a factor of about two.

Stereospecific preparation of amines has been disclosed. For example, *Tetrahedron Letters*, 1981, 22(28), 2633, describes the asymmetric synthesis of the cis-2-substituted cyclohexamines of the general formula

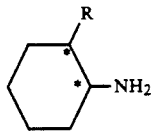

wherein the asterisks indicate chiral centers and the R and NH$_2$ substituents are in the cis orientation. Also, *Bulletin de la Societe Chimique de France*, 1970, 12, 4439, describes a study of the reaction products of the asymmetric synthesis of alpha-substituted ethylamines having the general formula

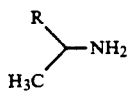

wherein the R group is, for example, ethyl or isopropyl. However, these articles do not disclose or suggest that such techniques would be applicable to compounds of the present invention.

SUMMARY OF THE INVENTION

The present invention relates to a process for producing compounds of the general formula 3

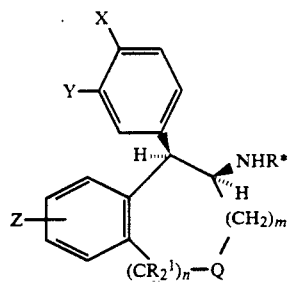

wherein:
R* is

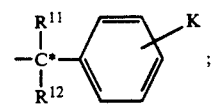

Q is methylene, —O— or —S—;

m and n are independently variable and may each have a value of 0, 1 or 2, with the provisos that the sum of m and n is not greater than 3, that m may not equal zero when Q is —O— or —S—, and that when Q is —CH$_2$—, m and n cannot both be zero;

X is hydrogen, alkyl, hydroxy, alkoxy or trifluoromethyl;

Y is hydrogen, hydroxy, alkoxy, —OC(O)NR$^2$R$^3$, —OC(O)—R$^9$, —N(R$^1$)$_2$, —NHC(O)R$^1$ or —OP(O)(OH)OR$^1$;

Each R$^1$ independently is H or alkyl;

R$^2$ and R$^3$ are the same or different and each may be hydrogen (provided that both are not hydrogen), alkyl, aralkyl, cycloalkyl, aryl, hydroxyalkyl, or alkoxyalkyl;

in addition, when one of R$^2$ and R$^3$ is as defined above, the other may be —R$^4$NR$^5$R$^6$ {wherein R$^4$ is alkanediyl, R$^5$ is hydrogen or alkyl and R$^6$ is alkyl, or R$^5$ and R$^6$ together with the nitrogen atom to which they are attached form a 1-azetidinyl, 1-pyrrolidinyl, 1-piperidinyl, 1-(4-alkylpiperazinyl), 4-morpholinyl or 1-(hexahydroazepinyl) group};

in further addition, R$^2$ and R$^3$ together with the nitrogen atom may form a 1-azetidinyl, 1-pyrrolidinyl, 1-piperidinyl, 4-morpholinyl, 1-(4-alkylpiperazinyl), 1-(4-alkoxyalkylpiperazinyl), 1-(4-hydroxyalkylpiperazinyl), 1-(3-hydroxyazetidinyl), 1-(3-alkoxyazetidinyl), 1-(-hydroxypyrrolidinyl), 1-(3-alkoxypyrrolidinyl), 1-(3- or 4-hydroxypiperidinyl), 1-(3- or 4-alkoxypiperidinyl), 1-(4-oxopiperidinyl) or 1-(3-oxopyrrolidinyl) ring;

in still further addition, when R$^2$ is hydrogen, R$^3$ may be —CHR$^7$CO$_2$R$^8$, wherein R$^7$ and R$^8$ are the same or different and each is hydrogen, alkyl or aralkyl;

R$^9$ is alkyl, aralkyl, aryl, alkoxyalkyl, aryloxyalkyl, aralkoxyalkyl, cycloalkylalkyl, alkoxycarbonylalkyl, cycloalkyl, 1-adamantyl, cycloalkoxyalkyl, alkoxy, aralkyloxy, cycloalkoxy, aryloxy or —CHR$^7$NHR$^8$; and Z is X as defined above, amino, alkylamino or —NHC(O)R$^{10}$ {wherein R$^{10}$ is hydrogen, alkyl or aryl};

R$^{11}$ is H or alkyl;

R$^{12}$ is alkyl;

with the proviso that R$^{11}$ and R$^{12}$ are different; and

3

K is hydrogen, alkoxy, hydroxy, arloxy, aralkyloxy, or alkyl;
said process comprising:
A. reducing compounds of the general formula 2

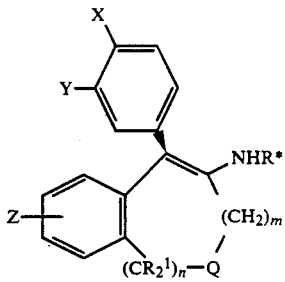

in the presence of a reducing agent, $H_2$ in the presence of catalyst, or a dissolving metal and acid;
B. followed preferably by isolation of compound 3.

A key feature of the present invention is the use of $R^*$ which must have a chiral center due to $R^{11}$ and $R^{12}$ not being identical. $R^{11}$ and $R^{12}$ are chosen based on the desired absolute stereochemistry of the final product.

In a preferred embodiment of the invention, said reducing agent is $NaCNBH_3$, $NaBH_4$, t-butyl amine borane (TBAB) or Zn dust. In one preferred embodiment of the invention, the cis amine of formula 3 is converted to the trans amine of formula 4

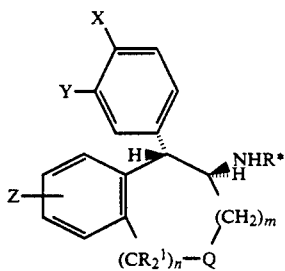

using a strong base.

Another preferred embodiment of the invention further comprises producing compound 2 from a compound of formula 1

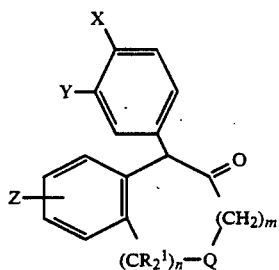

by reacting compound 1 with an optically active amine of the formula $H_2NR^*$ wherein all the substituents are as previously defined.

Still another preferred embodiment of the invention comprises removing the $R^*$ group from the trans amine of formula 4 and replacing it with an H to produce a compound of the general formula 5

4

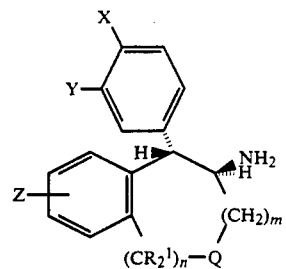

wherein the definitions are the same as for compound 3.

DETAILED DESCRIPTION OF THE INVENTION

When utilized herein, the terms below, unless otherwise indicated, have the following scope:

halogen—represents fluoro, chloro, bromo and iodo;

alkyl—represents straight or branched carbon chains, having from 1 to 6 carbon atoms;

hydroxylalkyl—represents an alkyl group as defined above in which a hydroxy group is substituted for one of the hydrogen atoms;

haloalkyl—represents alkyl as defined above wherein one of the hydrogen atoms is replaced by a halogen as defined above;

alkylamino—represents an amino, $NH_2$ or $NH_3^+$ group in which one or more of the hydrogens is substituted with an alkyl group as defined above;

cycloalkyl—represents a saturated carbocyclic ring having from 3 to 6 carbon atoms;

cycloalkylalkyl—represents an alkyl group as defined above in which a cycloalkyl group as defined above is substituted for one of the hydrogen atoms;

alkoxy—represents an alkyl having from 1 to 6 carbon atoms attached to a molecule by an oxygen atom (—O—alkyl);

alkoxyalkyl—represents an alkyl group as defined above in which an alkoxy group is substituted for one of the hydrogen atoms (alkyl—O—alkyl);

cycloalkoxyalkyl—represents a cycloalkyl as defined above in which an alkoxy group, as defined above, is substituted for one of the hydrogen atoms (cycloalkyl—O—alkyl);

cycloalkoxy—represents a cycloalkyl as defined above, which is attached to a molecule by an oxygen atom (—O—cycloalkyl);

aryl—represents a carbocyclic group containing from 6 to 15 carbon atoms and having at least one aromatic ring (e.g., a phenyl or fused benzene ring) with all available substitutable carbon atoms of the carbocyclic group being intended as possible points of attachment, said carbocyclic group being optionally substituted with 1 to 3 groups, each of which is independently selected from halo, alkyl, hydroxy, alkoxy, phenoxy, amino or alkylamino. Preferred aryl groups are phenyl and 2,4-dimethylphenyl;

aralkyl—represents an aryl as defined above in which an aryl group as defined above is substituted for one of the alkyl hydrogen atoms;

aryloxy—represents an aryl as defined above, which is attached to a molecule by an oxygen atom (—O—aryl);

aryloxyalkyl—represents an alkyl group as defined above in which an aryloxy group as defined above is substituted for one of the alkyl hydrogen atoms;

aralkyloxy—represents an aralkyl as defined above, which is attached to a molecule by an oxygen atom (—O—aralkyl);

aralkoxyalkyl—represents an alkyl group as defined above in which an aralkyloxy group as defined above is substituted for one of the alkyl hydrogen atoms;

alkoxycarbonylalkyl—represents an alkyl group as defined above in which a group alkyl—O—(CO)— is substituted for one of the alkyl hydrogen atoms, i.e., a group alkyl—O—(CO)—alkyl—;

alkanediyl—represents divalent, saturated, straight and branched hydrocarbon chains, preferably containing 1 to 8 carbon atoms.

Reaction Scheme 1 below illustrates the various aspects of the process of invention. This invention is directed at producing compound 3. This intermediate then may be utilized to produce a biologically active enantiomer of hexahydrobenzo[d]naphtho[2,1-b]azepines as the predominant reaction product without significant formation of the less active enantiomers. In the following description, the definitions of $R^1$, $R^2$, $R^3$, $R^4$, $R^5$, $R^6$, $R^7$, $R^8$, $R^9$, $R^{10}$, $R^{11}$, $R^{12}$, Q, W, X, Y, Z, m and n are as defined above unless otherwise indicated.

In step I, a compound of formula 1, which may be obtained as disclosed in European Patent Application No. 230270, is reacted with a compound of the general formula H₂NR* in a suitable solvent, preferably an organic inert solvent, e.g. toluene or benzene. A key feature of the present invention is the use of R* which must have a chiral center due to $R^{11}$ and $R^{12}$ not being identical. $R^{11}$ and $R^{12}$ are chosen based on the desired absolute stereochemistry of the final product. The temperature of the reaction may be room temperature to 150° C., preferably 80°–120° C., more preferably about 110° C., and the reaction is allowed to proceed to the desired completion, e.g. for from about 0.5 to 5 hours, preferably about 1.5 hours.

In step II, compound 2 is reacted with a suitable reducing agent, H₂ in the presence of catalyst, or a dissolving metal and acid, preferably with a reducing agent, under acidic conditions (e.g., pH 3 to 6.5, preferably pH about 5.2). Suitable reducing agents include NaCNBH₃, NaBH₄, t-butyl amine borane and Zn dust. Suitable catalysts include Pd, Ni, and Rh. Suitable acids are any acids which provide sufficient H⁺ ions to attain the desired pH and to reduce the double bond. The Scheme 1

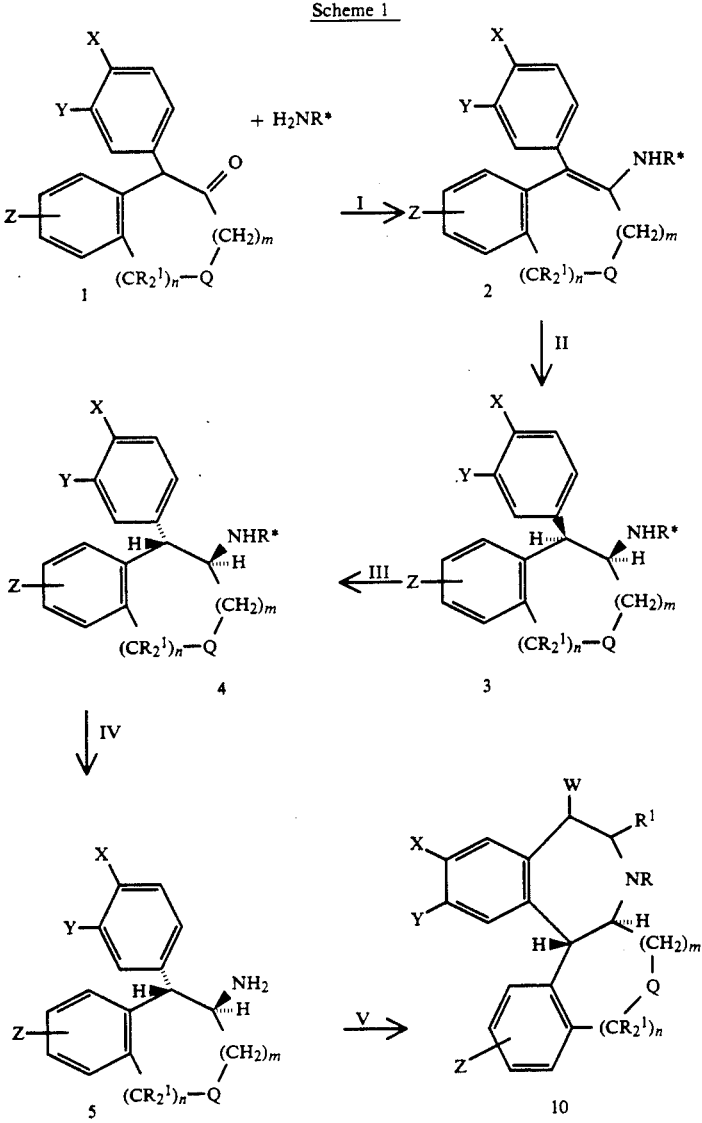

preferred acid is acetic acid. The reaction takes place at any suitable temperature, e.g., from 0° to 50° C., preferably at room temperature. The reaction proceeds to desired completion, e.g., for from 3 to 24 hours, preferably from 6 to 24 hours, and most preferably for about 18 hours.

In step III, a compound of formula 3 (the cis amine) is epimerized to the trans amine (formula 4). A compound of formula 3 is reacted with a suitable strong base in a suitable solvent at any suitable temperature, e.g., 0° to 25° C., preferably about 0° C. The reaction proceeds to desired completion, typically in about 15 minutes to 2 hours, preferably about 30 minutes. Suitable strong bases include KO—t—Bu, KOH, methoxide, e.g., sodium methoxide, and NaOH, preferably KO—t—Bu and suitable solvents include polar organic solvents such as dimethylformamide (DMF) and dimethylsulfoxide (DMSO).

In step IV, the R* group of the transamine of formula 4 is removed catalytically using $H_2$ gas to give a compound of formula 5. The reaction takes place under $H_2$ gas at atmospheric pressure to about 100 psi, at a suitable temperature, e.g., from 0° to 100° C., preferably at 25° C. The reaction proceeds to desired completion, typically for a period of from 1 hour to 7 days, preferably 1 to 7 days, more preferably about 3 to 4 days in the presence of a suitable catalyst. Preferred catalysts include Pd and Ni.

Step V represents the conversion of compounds of formula 5 to compounds of formula 10 as described in European Patent Application No. 230270.

EXAMPLE 1

3,4-Dihydro-1-(3-methoxyphenyl)naphthalene

A solution of 50 g (0.27 moles) 3-bromoanisole in 200 mL ether was added to 6.5 g (0.27 mole) magnesium turnings at a rate which maintained gentle reflux. After the addition was complete, the solution was refluxed for 2 hours, then cooled to room temperature. A solution of 36 g (0.24 moles) α-tetralone in 100 mL ether was added over one hour, with occasional cooling to maintain the reaction temperature at 20°–25° C. Thereafter, the reaction was stirred at room temperature overnight. The reaction was quenched with 1M HCl until acidic and the layers were separated. The aqueous layer was extracted with two 500 mL portions of ether. The combined ether layers were washed with 100 mL water, dried over magnesium sulfate, and evaporated to an oil. This was dissolved in 450 mL dry toluene containing 20 mg p-toluenesulfonic acid and refluxed overnight in a Dean-Stark apparatus. After cooling to room temperature, the solution was washed with 5% sodium bicarbonate, dried over magnesium sulfate, and evaporated. The residual oil was distilled under reduced pressure to give 36.8 g (60%) of the desired olefin. BP (0.5 mm) 158°–162° C. Analysis: Calculated for $C_{17}H_{16}O$: C,86.44; H6.83; found: C,86.45, H6.89.

EXAMPLE 2

3,4-Dihydro-1-(3-methoxyphenyl)-2(1H)naphthalenone

To a two-phase mixture of 82.2 grams (0.348 moles) of the above material, 41.6 grams (0.495 moles) sodium bicarbonate, 390 mL water, and 910 mL methylene chloride at 5° C. was added 82.6 grams of 80–85% m-chloroperbenzoic acid, added portion-wise over 25 minutes. The resulting mixture was stirred at 0°–5° C. for 2 hours. The layers were separated, and the aqueous layer was extracted with 250 mL methylene chloride. The combined organic layers were washed with 350 mL 10% sodium carbonate followed by 300 mL water. After drying over magnesium sulfate, the solvent was removed under vacuum to obtain a yellow oil. This was dissolved in 800 mL ethanol to which was then added a solution of 61.8 grams 87% aqueous potassium hydroxide in 160 mL water. The resulting dark solution was stirred at room temperature for four hours. The pH of the solution was adjusted to 7 by cautious addition of concentrated HCl with ice-cooling, and then the solvent was removed under vacuum. The resulting slurry was dissolved in 300 mL water and extracted with two 500 mL portions of ether. The combined ether layers were dried over magnesium sulfate and evaporated to obtain 89 grams of a brown oil. This was dissolved in 800 mL toluene containing 0.3 grams p-toluenesulfonic acid, and the resulting mixture was refluxed in a Dean-Stark apparatus for 8 hours. After cooling, the solution was washed with two 200 mL portions of 5% sodium bicarbonate, dried over magnesium sulfate, and evaporated to give 84.3 grams of a brown oil. This was purified by HPLC over silica gel, eluting with 1% ethyl acetate in hexane to give 55.45 grams of the desired ketone. IR (neat) 1718 cm$^{-1}$. A portion was converted to its 2,4-dinitrophenylhydrazone, mp=161°–161.5° C. (ethanol). Analysis calculated for $C_{23}H_{20}N_4O_5$: C,63.88, H,4.66, N,12.96, found: C,64.10, H,4.65, N.12.92.

EXAMPLE 3

(S)-3,4-Dihydro-1-(3-methoxyphenyl)-N-(1'-phenylethyl)-2-naphthaleneamine

To a solution of 55.45 grams (0.22 mol) of the above ketone in 800 mL toluene was added 31.8 mL (0.242 moles) of 98% (S)-(—)-α-methylbenzylamine, and the resulting mixture was refluxed in a Dean-Stark apparatus for 1.5 hours. An additional 4.63 mL 98% (S)-(—)-α-methylbenzylamine was added, and refluxing was continued for another 1.5 hours. The solvent was removed under vacuum at 55° C. to give 83.63 grams of crude enamine, which was used directly in the following step. IR (neat) 3390, 1615, 1600, 1570, 1490, 1390, 1285, 1210, 740, 700 cm$^{-1}$.

EXAMPLE 4

1(S),2(S),1'(S)-1-(3-Methoxyphenyl)-N-(1'-phenylethyl)-1,2,3,4,tetrahydro-2-naphthalenamine The above enamine was taken up in 800 mL of absolute ethanol, and 14.54 grams (.22 mol) sodium cyanoborohydride was added followed by 12.56 ml (.22 moles) glacial acetic acid. The resulting mixture was stirred at room temperature overnight. The reaction mixture was brought to pH 2 with 1M HCl and stirred for 45 minutes. After adjusting the pH to 8 with 25% sodium hydroxide, the ethanol was removed under reduced pressure, and the residue was extracted with two 450 mL portions of ether. The ether was dried over magnesium sulfate and evaporated to give 81.42 grams of viscous oil. This was purified by HPLC over silica gel eluting with 45:40:15 hexane:methylene chloride:ethyl acetate to give 76.42 grams of a mixture of diastereomeric amines.

To a solution of the above diastereomeric mixture in 2:1 DMSO:DMF at 0° C. was added 49.2 grams (.44 moles) potassium t-butoxide. After stirring 30 minutes at 0° C., the reaction was quenched with 1500 mL of saturated sodium bicarbonate. The mixture was extracted with three 600 mL portions of ether. The combined organic layers were washed with two 300 mL portions of water, dried over magnesium sulfate, and evaporated to give 73.61 grams of yellow oil. TLC and NMR indicated that this was the desired amine containing ~5% of the 1(R),2(R),1'(S) isomer. $^1$H NMR (200 MHz, CDCl$_3$) δ1.17 (d,3H,J=6.5 Hz, H-2'), 1.60 (m,1H,H-3,equatorial), 1.85 (m,1H,H-3,axial), 2.85 (tr,2H,J=7 Hz,H-4), 2.97 (dtr,1H,J=3,7 Hz,H-2), 3.79 (q,1H,J=6.5 Hz, H-1'), 4.03 (d,1H,J=6.5 Hz,H-1), 6.55 (m,1H,H-10), 6.61 (m,1H,H-14), 6.75 (m, 1H,H-12), 6.86 (m,1H,H-8), 7.00-7.38 (m,9H,H-5,6,7,13,2'',3'',4'',5'',6'')

EXAMPLE 5

(+)-1(S),2(S)-1-(3-Methoxyphenyl)-1,2,3,4,tetrahydro-2-naphthalenamine

A solution of the above amine in 250 mL ethanol was poured into 600 mL 4N sulfuric acid containing 4.5 grams 20% palladium hydroxide on carbon. The resulting mixture was hydrogenated in a Parr shaker under 50 PSI hydrogen at room temperature for four days. The reaction was filtered through celite, and the celite cake was washed with dilute sulfuric acid and with ethanol. The combined filtrates were brought to pH 10 with 20% sodium hydroxide and then extracted with two 500 mL portions of ether. After drying over magnesium sulfate, the ether was removed under vacuum to obtain 34.06 grams of yellow oil. This was purified by HPLC over silica gel to obtain 28.56 grams of solid product, mp=56.5°-57.5° C., [α]$_D$+40.9 in ethanol.

EXAMPLE 6

(+)-1(S),2(S)-N-(2',2'-Diethoxyethyl)-1-(3-methoxyphenyl)-1,2,3,4,tetrahydro-2-naphthalenamine A mixture of 28.46 grams (0.112 moles) of the above amine, 20.3 mL (0.135 moles) of 97% bromoacetaldehyde diethylacetal, 77.5 grams (0.562 moles) potassium carbonate, and 450 mL DMF was heated under nitrogen at 125° C. for 20 hours. After cooling, the mixture was diluted with 1500 mL ether, washed with three 400 mL portions of water, dried over magnesium sulfate, and evaporated to give 43.76 grams of a dark yellow oil. This was purified by chromatography over flash grade silica gel (7.5 inches dry in a 50 mm column) eluting first with 25% ethyl acetate in hexane to remove impurities followed by 100% ethyl acetate to elute the product in slightly impure form. A second chromatography eluting with 65% ethyl acetate in hexane gave 29.79 grams of the pure trans aminoacetal as an oil. C,H,N analysis, calculated for C$_{23}$H$_{31}$NO$_3$: C,74.76, H,8.46, N,3.79, found: C,74.60, H,8.59, N,3.75. [α]$_D$+70.9.

EXAMPLE 7

6a(S),13b(S)-5,6,6a,13b-Tetrahydro-12-methoxybenzo[d] naptho[2,1-b] azepine

To a solution of 280 mL of methanesulfonic acid in 50 mL methylene chloride at 0° C. was added a solution of 29.16 grams (0.079 moles) of the above acetal in 900 mL methylene chloride over one hour. The resulting solution was stirred overnight while coming to room temperature. The reaction mixture was quenched by pouring into 3800 mL saturated aqueous sodium bicarbonate. The layers were separated, and the aqueous layer was extracted with two 1000 mL portions of ethyl acetate. The combined organic layers were dried over magnesium sulfate and evaporated to give 23.14 grams of yellow solid. $^1$H NMR (200 MHz, CDCl$_3$) δ1.50 (m,1H,H-6eq), 2.30 (m,1H,H-6ax), 2.76 (m,3H, H-5,6a), 3.60 (s,3H,12-CH$_3$O), 5.33 (d,1H,J=10 Hz,H-9), 5.99 (d,1H,J=3 Hz,H-13), 6.19 (dd,1H,J=5.5 Hz,10 Hz,H-8), 6.64 (dd,1H,J=3,8 Hz,H-11), 7.1-7.3 (m,5H,H-1,2,3,4,10). Mass spec (m/e) 277.0 (present).

EXAMPLE 8

(−)-6a(S),13b(R)-5,6,6a,7,8,13b-Hexahydro-12-methoxybenzo[d] naptho[2,1-b] azepine The above crude product was dissolved in 1100 mL absolute ethanol. To this was added 5.22 grams (0.079 moles) sodium cyanoborohydride followed by 4.75 mL (0.083 moles) glacial acetic acid. The resulting mixture was stirred overnight at room temperature. The solution was adjusted to pH 2 by addition of 1M HCl then stirred 30 minutes. After adjusting the pH to 8 with 25% sodium hydroxide, the ethanol was removed under vacuum, and 250 mL water was added. The aqueous mixture was extracted with three 350 mL portions of ether. The combined ether layers were washed with two 150 mL portions of water, dried over magnesium sulfate, and evaporated to obtain 22.54 grams of a yellow foam. This was purified by flash chromatography over silica gel, eluting with 9% methanol in methylene chloride. After evaporating those fractions shown to contain product by TLC, the combined residues were again chromatographed eluting with 10% methanol-methylene chloride to give 12.52 grams of the desired product as an off-white solid, mp=51.0°-54° C. Analysis calculated for C$_{19}$H$_{21}$NO: C,81.68, H,7.58, N,5.01 found: C,81.39, H,7.49, N,5.00. [α]$_D$−268.2.

EXAMPLE 9

(−)6a(S),13b(R)-11-Chloro-5,6,6a,7,8,13b-Hexahydro-12-methoxy-benzo[d] naptho[2,1-b] azepine To a solution of 8.71 grams (0.0312 moles) the above product in 525 mL methylene chloride at 0° C. under nitrogen was added 40.5 mL (0.0405 moles) of 1M sulfuryl chloride, added dropwise over 30 minutes. The resulting mixture was stirred overnight while coming to room temperature. The reaction was quenched with 90 mL water and neutralized with 90 mL saturated sodium bicarbonate. The layers were separated, and the aqueous layer was extracted with 125 mL methylene chloride. The combined organic layers were washed with 200 mL water, dried over magnesium sulfate, and evaporated to give 10.34 grams of a tan foam. This was purified by flash chromatography, eluting with 10% methanol-methylene chloride to give 7.48 grams product. $^1$H (200 MHz, CDCl$_3$) δ1.50 (m,1H,H-6eq), 2.30 (m,1H,H-6ax), 2.76 (m,3H,H-5,6a), 3.52 (s,3H, 12-CH3O), 5.22 (d,1H,J=10 Hz,H-9), 5.99 (s,1H,H-13), 6.23 (dd,1H,J=10 Hz,5.5 Hz,H-8), 7.1-7.3 (m,6H), 1.70 (m,1H), 2.00 (m,1H), 2.75 (m,5H), 2.33 (m,2H), 3.53 (s,1H, 12-CH3O), 4.51 (d,1H,J=8 Hz,H-13b), 6.01 (s,1H,H-13), 7.15 (m,6H,H1,2,3,4,10), high resolution mass spectrum calculated for C$_{19}$H$_{21}$ClNO: 314.1312, found: 314.1320, [α]$_D$−216.7.

EXAMPLE 10

6a(S),13b(S)-11-Chloro-5,6,6a,7,8,13b-Hexahydro-12-methoxy-7-methyl-benzo[d] naptho[2,1-b] azepine To a cooled solution of 7.07 g (0.0225 moles) the above compound in 110 mL dry DMF was added 2.16 mL 90% formic acid and 1.90 mL (0.0258 moles) 38% aqueous formaldehyde. The reaction mixture was stirred at 80° C. for 2.5 hours, cooled to room temperature, and then quenched with 100 mL water and 20 mL 20% sodium hydroxide. The reaction was extracted with two 175 mL portions of ether. The ether extracts were washed with two 75 mL portions of water, dried over magnesium sulfate, and evaporated under reduced pressure to give 6.81 grams of crude product. Purification by flash chromatography, eluting with 20% methanol-ethyl acetate gave 5.6 g (76%) of the desired compound. $[\alpha]_D - 187.3$. Analysis calculated for $C_{20}H_{23}NOCl$: C,73.27, H,6.76, N,4.27, found: C,73,23, H,6.81, N,4.16, High resolution mass spectrum calculated for $C_{20}H_{23}NOCl$: 328.1468, found: 318.1483.

EXAMPLE 11

6a(S),13b(S)-5,6,6a,7,8,13b-Hexahydro-7-methyl-11-chloro-12-methoxy-9H-benzo[d]naptho[2,1-b]azepine To 85 mL methylene chloride under nitrogen was added 28.4 mL (0.0284 moles) 1.0M boron tribromide in methylene chloride. The resulting solution was cooled to −78° C., and a solution of 4.663 grams (0.0142 moles) of the above compound was added slowly with stirring. The reaction was then stirred four hours while coming to room temperature. After cooling to 0° C., 9 ml methanol was added, and the mixture was stirred 30 minutes while coming to room temperature. An additional 15 mL methanol was added, and the mixture was stirred another 15 minutes. The solvent was removed under vacuum to obtain the crude hydrobromide salt. The product was dissolved in 72 mL DMF at 70° C. and then added slowly to a 70° C. solution of 14.4 grams sodium bicarbonate in 295 mL water. Precipitation was immediate. After stirring 15 minutes, the mixture was chilled in an ice bath with stirring, and the precipitate was collected by vacuum filtration. The wet solid was digested with 25 mL acetonitrile at 70° C. for 15 minutes. After chilling, the precipitate was again collected by vacuum filtration, washed with cold ether, and dried overnight under vacuum at 85° C. to give 3.15 grams of product with $[\alpha]_D - 199.4$. A second acetonitrile digestion yielded 2.62 grams of product with $[\alpha]_D - 209.7$. Further digestion or purification did not change the rotation. Analysis calculated for $C_{19}H_{20}ClNO$: C,72.72, H,6.42, N,4.46, found: C,72.60, H,6.40, N,4.46.

We claim:

1. A process for producing compounds of the formula

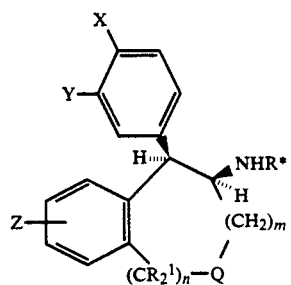

wherein:
R* is

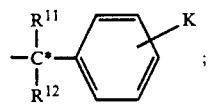

Each $R^1$ is independently H or alkyl;

Q is methylene, —O— or —S—;

m and n are independently variable and may each have a value of 0, 1 or 2 with the provisos that the sum of m and n is not greater than 3, that m may not equal zero when Q is —O— or —S—, and that when Q is —CH$_2$—, m and n cannot both be zero;

X is hydrogen, alkyl, hydroxy, alkoxy or trifluoromethyl;

Y is hydrogen, hydroxy, alkoxy, —OC(O)NR$^2$R$^3$, —OC(O)—R$^9$, —N(R$^1$)$_2$, —NHC(O)R$^1$ or —OP(O)(OH)OR$^1$;

R$^2$ and R$^3$ are the same or different and each may be hydrogen (provided that both are not hydrogen), alkyl, aralkyl, cycloalkyl, aryl, hydroxyalkyl, or alkoxyalkyl;

in addition, when one of R$^2$ and R$^3$ is as defined above, the other may be —R$^4$NR$^5$R$^6$ {wherein R$^4$ is alkanediyl, R$^5$ is hydrogen or alkyl and R$^6$ is alkyl, or R$^5$ and R$^6$ together with the nitrogen atom form a 1-azetidinyl, 1-pyrrolidinyl, 1-piperidinyl, 1-(4-alkylpiperazinyl), 4-morpholinyl or 1-(hexahydroazepinyl) group};

in further addition, R$^2$ and R$^3$ together with the nitrogen atom may form a 1-azetidinyl, 1-pyrrolidinyl, 1-piperidinyl, 4-morpholinyl, 1-(4-alkylpiperazinyl), 1-(4-alkoxyalkylpiperazinyl), 1-(4-hydroxyalkylpiperazinyl), 1-(3-hydroxyazetidinyl), 1-(3-alkoxyazetidinyl), 1-(-hydroxypyrrolidinyl), 1-(3-alkoxypyrrolidinyl), 1-(3- or 4-hydroxypiperidinyl), 1-(3- or 4-alkoxypiperidinyl), 1-(4-oxopiperidinyl) or 1-(3-oxopyrrolidinyl) ring;

in still further addition, when R$^2$ is hydrogen, R$^3$ may be —CHR$^7$CO$_2$R$^8$, wherein R$^7$ and R$^8$ are the same or different and each is hydrogen, alkyl or aralkyl;

R$^9$ is alkyl, aralkyl, aryl, alkoxyalkyl, aryloxyalkyl, aralkoxyalkyl, cycloalkylalkyl, alkoxycarbonylalkyl, cycloalkyl, 1-adamantyl, cycloalkoxyalkyl, alkoxy, aralkoxy, cycloalkoxy, aryloxy or —CHR$^7$NHR$^8$; and Z is X as defined above, amino, alkylamino or —NHC(O)R$^{10}$ {wherein R$^{10}$ is hydrogen, alkyl or aryl};

R$^{11}$ is H or alkyl;

R$^{12}$ is alkyl;

with the proviso that R$^{11}$ and R$^{12}$ are different; and

K is hydrogen, alkoxy, hydroxyl, arloxy, aralkoxy, or alkyl;

said process characterized by reducing compounds of the formula 2

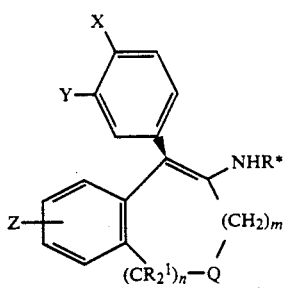

wherein the definitions are the same as for formula 3, in the presence of a reducing agent, $H_2$ in the presence of catalyst, or a dissolving metal and acid.

2. The process of claim 1 further characterized by said reducing agent being selected from $NaCNBH_3$, $NaBH_4$, t-butyl amine borane, or zinc dust.

3. The process of claim 1 further characterized by converting of the cis amine of formula 3 to the trans amine of formula 4

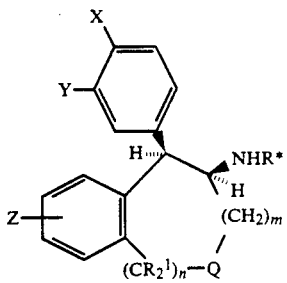

with a base.

4. The process of claim 1 further characterized by reacting a compound of formula 1

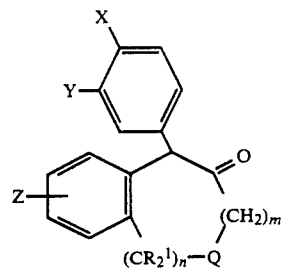

by reacting the compound of formula 1 with an optically active amine of the formula $H_2NR^*$ to produce a compound of formula 2.

5. The process of claim 1 further characterized by the process of replacing the $R^*$ group of the trans amine of formula 4 with a hydrogen to produce a compound of formula 5

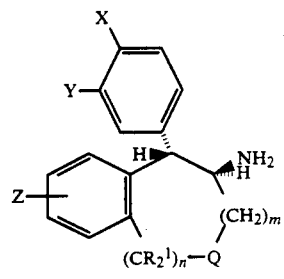

* * * * *